United States Patent [19]

Larkin

[11] Patent Number: 4,588,834

[45] Date of Patent: May 13, 1986

[54] PROCESS FOR CARBONYLATION OF OLEFINS TO CARBOXYLIC ACIDS AND ESTERS

[75] Inventor: John M. Larkin, Austin, Tex.

[73] Assignee: Texaco Inc., White Plains, N.Y.

[21] Appl. No.: 657,565

[22] Filed: Oct. 4, 1984

[51] Int. Cl.$^4$ .............................................. C07C 67/38
[52] U.S. Cl. .................................... 560/233; 562/522
[58] Field of Search ......................... 560/233; 562/522

[56] References Cited

U.S. PATENT DOCUMENTS

| | | | |
|---|---|---|---|
| 3,816,488 | 6/1974 | Craddock | 560/233 |
| 3,816,489 | 6/1974 | Craddock | 560/233 |
| 3,944,604 | 3/1976 | Hershman | 560/233 |
| 3,976,670 | 8/1976 | Fanning | 560/233 |
| 4,238,357 | 12/1980 | Pesa | 560/233 |

*Primary Examiner*—Michael L. Shippen
*Attorney, Agent, or Firm*—Jack H. Park; Kenneth R. Priem; Cynthia L. Kendrick

[57] ABSTRACT

Carboxylic acids, for example n-butyric and isobutyric are prepared from an olefin such as propylene in a process comprising passing a liquid feed consisting of an olefin, an alkyl halide or heterocyclic amine promoter, a protonic coreactant, and a low concentration of a soluble metal catalyst, optionally in the presence of a solvent, and a gas consisting essentially of carbon monoxide over a carbon bed maintained at a temperature of from about 200° C. to about 400° C. and a pressure of from about 500 psi to about 4000 psi or greater.

17 Claims, No Drawings

PROCESS FOR CARBONYLATION OF OLEFINS TO CARBOXYLIC ACIDS AND ESTERS

FIELD OF THE INVENTION

This invention relates to reactions wherein an olefin is reacted with carbon monoxide over a carbon bed at elevated temperatures and pressures in the presence of soluble Ru, Ni or Co catalysts.

BACKGROUND OF THE INVENTION

There are processes in the art teaching the production of carboxylic acids and esters from olefins using a variety of catalyst systems. However, in these processes the catalyst is usually complex and the use of a carbon bed is not suggested.

U.S. Pat. No. 4,303,589 discloses a process for hydroesterification of internal olefins to produce carboxylic esters of high normality over a cobalt catalyst at 170°–200° C. and 1200 to 1800 psi. High concentrations of cobalt are required.

U.S. Pat. No. 2,739,169 discloses a method for the preparation of propionic acid which comprises reacting diethyl ether, water and carbon monoxide in the presence of a three component catalyst generated from a three component mixture comprising nickel chloride, hexahydrate, copper and sodium iodide. This process does not address production of iso and n-butyric acids and esters.

In Journal of Molecular Catalysts, 10 (1981) 161–170, Caminato and Toniolo discuss the hydrocarboalkoxylation of propene promoted by a palladium platinum complex catalyst precursor at 100° C. to 110° C. with high selectivity toward the branched isomer when a solvent is added to the alkanol.

The reaction of olefins with carbon monoxide and water in the presence of a variety of transition metal catalysts is disclosed in "Mechanistic Pathways in the Catalysis of Olefin Hydrocarboxylation by Rhodium, Iridium, and Cobalt Complexes", CATAL. REV. SCI. ENG., 23 (1 and 2), 89–100 (1981).

In U.S. Pat. No. 3,917,677 carboxylic acid esters are prepared by reacting ethylenically unsaturated compounds with carbon monoxide and alcohols in the presence of a catalyst solution essentially comprising a rhodium component and a tertiary organophosphorous component, said solution being essentially free of halogen.

An article by Fenton entitled "Noble Metal Catalysis II Hydratocarbonylation Reaction of Olefins with Carbon Monoxide to Give Saturated Acids" in *J. Org. Chem.*, Vol. 38, No. 18, 3192 (1973) discloses a process for hydratocarbonylation of olefins with carbon monoxide to give saturated acids wherein the catalyst employed is a zero valent palladium phosphine complex.

For a general discussion of carbonylation of olefins see I. Wender and P. Pino, *Organic Synthesis via Metal Carbonyls*, Vol. 2, p. 233–296, John Wiley and Sons, N.Y., 1977.

It would be a considerable advance in the art to provide a catalyst system for preparation of carboxylic acids from olefins, methanol and carbon monoxide which uses much lower concentrations of soluble metal catalysts than used in prior art, which allows for ease of separation of catalyst and product and which produces a mixture of valuable chemicals such as n-butyric acid, isobutyric acid, acetic acid and methyl acetate. The isobutyric acid and esters are useful in preparation of methacrylic acid and esters. n-Butyric and isobutyric acid are useful for preparation of synthetic lubricants. Acetic acid has a myriad of industrial uses including the preparation of vinyl acetate, a useful monomer used for creating valuable polymers.

SUMMARY OF THE INVENTION

It has now been found that use of a low concentration of soluble Group VIII metal catalyst in combination with a promoter selected from the group consisting of alkyl halides and heterocyclic aromatic amines and a protonic coreactant over a carbon bed at elevated temperatures and pressures permits a good combination of products from olefins together with efficient product recovery and catalyst recycling.

DETAILED DESCRIPTION OF THE INVENTION

In the narrower practice of this invention, carboxylic esters are continuously prepared in good yield from an olefin and carbon monoxide by a process comprising the following steps: (a) Passing a solution consisting of an olefin, a promoter from the group consisting of an alkyl halide and a heterocyclic aromatic amine, a protonic coreactant, and a low concentration of a soluble metal species optionally in the presence of a solvent along with a gas consisting essentially of carbon monoxide over a carbon bed maintained at a temperature of from about 200° C. to about 400° C. or more and a pressure of from about 500 psi to about 4000 psi or greater and isolating said esters. The process is characterized by good productivity, especially with the ruthenium catalyst, easy recycle and easy separation.

The reaction can be illustrated by the following equation:

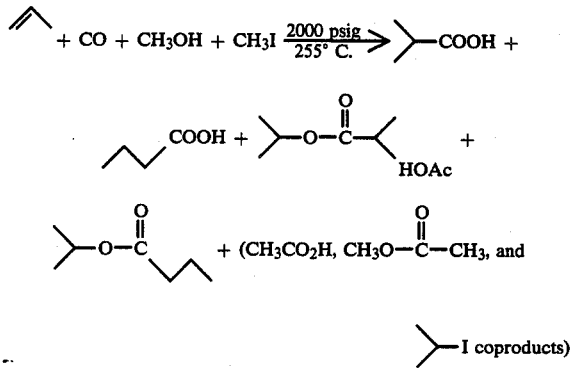

In order to present the inventive concept in the greatest possible detail to promote its understanding the following supplementary disclosure is submitted. The basic invention, improved upon here is practiced as follows:

Catalysts that are suitable in the practice of this invention contain a soluble Group VIII transition metal. Also necessary for this invention is a bed of carbon which preferably is activated and can be optionally washed. The soluble metal catalyst may be chosen from a wide variety of organic or inorganic compounds, complexes, etc, as will be shown and illustrated below. It is only necessary that the catalyst precursor actually employed contain certain Group VIII metals in a soluble state. It has been found that certain promoters and a protonic coreactant are necessary for the carbonylation to take place according to the general scheme outlined above.

The actual catalytically active species is unknown, but is believed to comprise a Group VIII metal in complex combination with a halide or amine promoter and a protonic coreactant in association with the activated carbon in the carbon bed.

The following discloses in greater detail the process of the invention:

The soluble metal catalyst precursors may take many different forms. Generally the metal species used are selected from the Group VIII transition metals. Effective metals would include Co, Ru, Fe, Ni, Rh, Pd, Os, Ir and Pt. The soluble Group VIII metal catalyst may be added to the reaction mixture in the form of a carbonyl as in the case of, for example, triruthenium dodecacarbonyl, dicobalt octacarbonyl, iron pentacarbonyl, nickel tetracarbonyl, diiron nonacarbonyl and tetracobalt dodecacarbonyl. Alternatively the Group VIII metal may be added as the salt of a mineral acid, as in the case of, for example, ruthenium trichloride, iron(II) iodide, iron(III) nitrate, cobalt(II) nitrate, cobalt(II) chloride and nickel(II) iodide, or as the salt of a suitable organic carboxylic acid, such as, for example cobalt(II) acetate, cobalt(III) acetate, Ni(II) propionate and Fe(II) naphthenate. The metal may furthermore be added to the reaction zone as a complex with a trisubstituted phosphorus compound or as a salt of an enolate. Here suitable examples include cobalt(III) 2,4-pentanedionate and dichlorotris(triphenylphosphine)ruthenium(II).

Preferred Group VIII soluble transition metal catalysts include carbonyls and halides. Among the particularly preferred are ruthenium chloride, ruthenium dodecacarbonyl and dicobalt octacarbonyl. The usefulness of these Group VIII transition metal precursors for carboxylic ester synthesis is illustrated by the accompanying Examples.

The Group VIII transition metal catalyst is passed in solution with other reactants, including an olefin such as propylene and a gas comprising essentially carbon monoxide along with the halide or amine promoter and a protonic coreactant over an activated carbon bed.

The promoter found necessary to effect the desired carbonylation should generally be present in an amount of 1-20 mole %. This promoting component of the catalyst system may consist of a halide compound that may be introduced into the reaction zone in liquid form, or gaseous form or dissolved in a suitable solvent or reactant. Satisfactory halide promoters include hydrogen halides, such as hydrogen iodide and aqueous hydriodic acid, alkyl halides containing 1 to 12 carbon atoms such as methyl iodide, ethyl iodide, 1-iodopropane, 2-iodobutane, 1-iodobutane, methyl bromide, ethyl bromide, and benzyl iodide, dihalomethanes such as diiodomethane as well as acyl halides such as acetyl iodide. Also suitable as halogen coreactants are the quaternary ammonium and phosphonium halides; examples include tetramethylammonium iodide and tetrabutylphosphonium iodide. Alkali and alkaline earth halides, such as cesium iodide, may also be used.

The lower alkyl iodide or bromide promoters containing 1-6 carbon atoms are the preferred coreactants for the carbonylation reaction of this invention. Most preferred is methyl iodide.

Alternatively the promoter may consist of a heterocyclic aromatic amine. Satisfactory amine promoters include pyridine, 4-picoline, 2-picoline, purine and 4-ethylpyridine. The preferred heterocyclic aromatic amines are pyridine, 4-picoline, 4-ethylpyridine and 2-picoline.

The gas which is reacted with the liquid feed and passed over the activated carbon bed in the process of this invention comprises essentially carbon monoxide. The carbon monoxide may be used in conjunction with up to 90% by volume of one or more other gases. These other gases may include one or more inert gases such as nitrogen, argon, neon and the like. Hydrogen may also be present in the carbon monoxide gas, but a part of the carbon monoxide reacts with the hydrogen thus rendering that part inactive for reaction with an alkanol to form a carboxylic acid.

As stated, a protonic coreactant is reacted with the propylene and CO in the process of this reaction. The protonic coreactant may consist of alcohol or water. It is believed this participates in the reaction by reacting with the metal carbonyl adduct of the propylene. The preferred protonic coreactant is methanol.

A solvent is generally not necessary for the practice of this invention since the low molecular weight olefins which are reactants and protonic coreactants serve as satisfactory solvents. A solvent could be used, however, if the transition metal compound or the halide promoter were only partially soluble in these reactants. In other cases a solvent might be used to aid in separation of products as for example by codistillation or by formation of an insoluble product layer. Solvents which could be used include compounds which are inert to the reaction conditions and which do not impede the desired reaction. Suitable solvents include aliphatic or aromatic hydrocarbons such as pentane, 2-methylhexane, cyclohexane, benzene, toluene, o-, m-, or p-xylene, and ethylbenzene, as well as aromatic or aliphatic ethers such as diphenyl ether, diethyl ether, p-dioxane, and tetrahydrofuron. Other solvents include aliphatic or aromatic ketones such as acetone, 4-methyl-2-pentanone, and acetophenone. Still other suitable solvents include esters of carboxylic acids such as alkyl acetates, propionates, octanoates and the like. Especially preferred solvents are those esters which are formed as minor coproducts during normal practice of this invention such as formed as a coproduct during reaction of methanol with carbon monoxide and propylene (e.g. methyl isobutyrate). Other solvents include carboxylic acids such as acetic, propionic, octanoic, and isobutyric acids. Water could also be used as a solvent.

The activated carbon bed over which is passed the liquid feed stream can be fixed or fluidized and is prepared from a porous solid. The density range of the solid should be about 0.03-2.5 $g/cm^3$. Preferred density range is 0.05-1.5 $g/cm^3$. A fixed carbon bed can be prepared from porous carbon by pyrolysis of amorphous carbon. Activated carbons of this type have surface areas of 200-2000 $m^2/g$. Carbons can be preformed of compacted granules, powders, or particles. Powdered sources are not preferred.

A fluidized carbon bed or ebullient carbon bed is prepared by providing agitated contact of the activated carbon particles with the mixture of reactant liquids and gases as for example suspending the carbon particles in the gas/liquid stream.

The activated carbon bed can optionally be washed to remove metallic components which may be present from the organic sources used to prepare the carbon. If washed, the treatment consists of a HF solution or $HNO_3$ solution where the ratio is about 600 to about 1000 ml of HNO₃ per 500 g carbon and the HNO₃ concentration in water is from about 2%–30%. If HF is used, the concentration in water should be from about 10–55%. Washing time may be from 5 minutes to 24 hours. Further, the acid washed carbon can be washed with H₂O to remove excess acid.

Suitable sources of activated carbon which could be used in the process of this invention consist of NORIT® RB-1 or SORBONORIT® B-3 activated carbon.

NORIT® and SORBONORIT® are registered trademarks of the American Norit Company. Another suitable activated carbon which could be used is CARBORUNDUM® GAC-616G. CARBORUNDUM® is a registered trademark of Kennecott Corporation. These activated carbons, prepared by the manufacturers according to procedures developed by them, are in the form of granules or pellets, and are described as generally having a surface area of 1000–1200 m²/g. Methods of manufacturing activated carbon are listed in the book: *Activated Carbon, Manufacture and Regeneration* by A. Yehaskel, Noyes Data Corporation, Park Ridge, N.J. 1978.

Where the reaction takes place using propylene, isobutyric acid and its ester, n-butyric acid and its ester and propionic acids are prepared in good yield with conversion of propylene ranging from about 10 to about 50% and selectivity to carboxylic acids reaching as high as 31%.

The major by-products of these carboxylic acid/ester syntheses are most commonly isobutyraldehyde, n-butyraldehyde and propionic acid which are, of course, also useful compounds and major articles of commerce. The butyraldehydes and other products can easily be separated from one another by conventional means, e.g. fractional distillation. If desired, the butyraldehydes can be oxidized to butyric acids by methods well-known in the art.

The quantity of soluble transition metal catalyst employed in the instant invention is not critical and may vary over a wide range. Metal concentrations could range from less than 5 (e.g. 1) to greater than 1000 ppm, depending on the activity of the metal species. In general, this improved process is desirably conducted in the presence of a catalytically effective quantity of the active metal species, in conjunction with a halide promoter, and optionally in the presence of a solvent which gives the desired products in reasonable yields. The reaction proceeds when employing as little as about 0.0001 weight percent, and even lesser amounts of Group VIII metal catalyst together with about 1.0–50 weight percent of a halide or amine promoter and 2–50 weight percent protonic coreactant, basis the total weight of the reaction mixture. The upper concentration is dictated by a variety of factors including catalyst cost, partial pressures of carbon monoxide, operating temperature etc. A soluble Group VIII metal catalyst concentration of from about 0.002 to about 0.02 weight percent metal in conjunction with an halide or aromatic amine promoter concentration of from about 5 to about 25 mole percent and a protonic coreactant concentration of 5 to 25 mole percent based on the total moles of reaction mixture is generally desirable in the practice of this invention.

The temperature range which can usefully be employed in these syntheses is a variable dependent upon other experimental factors, including the pressure, the concentration and the choice of the particular species of soluble Group VIII metal catalyst, among other things. The range of operability is from about 200° to 400° C. when superatmospheric pressures of carbon monoxide are employed. A narrow range of 240°–300° C. represents the preferred temperature range.

Superatmospheric pressures of 100 psi or greater lead to substantial yields of carboxylic acids by the process of this invention. A preferred operating range is from 500 psi to 4000 psi, although pressures above 4000 psi also provide useful yields of desired acetic acid.

In all these syntheses, the amount of carbon monoxide present in the reaction mixture should be sufficient to at least satisfy the stoichiometry of the desired carbonylation reaction.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees Celsius and all pressures in pounds per square inch gauge (psig).

Having described the inventive process, the following examples are submitted to supply specific and illustrative embodiments:

EXAMPLE I

In Examples I through III, a 25 cc reactor of Hastelloy construction filled with SORBONORIT® B-3 activated carbon was used. It has been disclosed that use of this reactor system and its associated metal conduits is known to provide low levels (<115 ppm) of soluble nickel species in addition to the metals which are added to the feed.

In Example I a liquid feed consisting of 635.04 g propylene, 234.2 g CH₃I, 320.4 g CH₃OH, and 0.30 g Ru₃(CO)₁₂ was pumped to the reactor at 8 ml/hr together with CO at 7 liters/hour. The reactor was maintained at 255° C. and 2000 psig throughout the 122 hour run. Effluent collected at 46 hours and at 97 hours contained the following organic components.

|  | 48 hours | 97 hours |
| --- | --- | --- |
| CH₃OH | 0.8 | 0.6 |
| CH₃OAc | 5.7 | 1.4 |
| CH₃—C—CH₃<br>　　｜<br>　　OH | 0.5 | 4.1 |
| HOAc | 42.5 | 37.5 |
| CH₃—CH—CH₃<br>　　　｜<br>　　　I | 9.0 | 10.2 |
| Isobutyric acid | 13.5 | 10.9 |
| n-butyric acid | 11.6 | 10.7 |
| isopropyl isobutyrate | 3.0 | 2.5 |
| isopropyl n-butyrate | 3.2 | 3.4 |
| propionic acid | ND | 1.0 |

Water and unknown compounds constituted the balance of the effluent.

An analysis of off-gas collected past the liquid effluent container showed the following components:
1.7% H₂
21.9% CO₂
0.6% CH₄

7.2% CO
61.8% propylene
21.1% $H_2O$

EXAMPLE II

A liquid feed consisting of 635 g propylene, 234.2 g methyl iodide, 320.4 g of methanol, and 0.40 g of $Co_2(CO)_8$ was supplied continuously to the reactor at the rate of 16.65 g/hr while CO was supplied at 2-3 liters/hr. Pressure was kept at close to 2100 psig but temperatures were deliberately varied. Effluent analyses at various temperatures showed the following quantities of butyric acids (iso and normal) and their esters:

| Temp. °C. | Isobutyric acid and n-butyric Acid and Esters |
| --- | --- |
| 245 | 0.8% |
| 275 | 3.1% |
| 285 | 6.0% |

Analysis of gas from the reactor collected past the point of liquid collection while the reactor was at 275° C. indicated the following:

| | | |
| --- | --- | --- |
| 0.1% $H_2$ | 56.6% CO | 6.9% $(CH_3)_2O$ |
| 0.1% $CO_2$ | 30.2% $C_3H_6$ | 0.5% isobutyraldehyde |
| 0.1% $CH_4$ | 2.1% $C_3H_8$ | 0.04% n-butyraldehyde |

This example illustrates that although soluble cobalt does catalyze the reaction between propylene and CO to provide butyric acids and esters, its activity is much lower than that of ruthenium. On the other hand, $C_4$ aldehydes are generated, and the selectivity for isobutyraldehyde is good.

EXAMPLE III

A liquid feed consisting of 842 g (10 moles) 1-hexene, 466 g (5 moles) of 4-picoline, 240 g (7.5 moles) of $CH_3OH$, 9.00 g (0.5 moles) $H_2O$, and 0.50 g (0.00146 moles) of $Co_2(CO)_8$ was conducted to the reactor at 6 ml/hr, and CO was supplied at 6 liters/hr. The reactor was maintained at 275° C. for 22 hours and at 250° C. for 22 hours more; pressure was kept at 3000 psig throughout the run.

Effluent analyses at 275° C. indicated about 0.8% methyl heptanoate.

What is claimed is:

1. A process for the continuous production of esters of carboxylic acids which comprises passing a liquid feed consisting of propylene, a promoter selected from the group consisting of halides and heterocyclic aromatic amines and a Group VIII soluble metal catalyst selected from the group consisting of compounds of ruthenium, nickel and cobalt and a protonic coreactant from the group consisting of alcohols and water, wherein the metal catalyst concentration ranges from 1 ppm to greater than 1000 ppm, optionally in the presence of a solvent and a gas comprising carbon monoxide over a carbon bed maintained at a temperature of 225°-350° C. and a pressure of from about 500 psi to 4000 psi.

2. The process of claim 1 wherein the halide promoter is selected from the group consisting of alkyl halides, hydrogen halides, and acyl halides.

3. The process of claim 2 wherein the alkyl halide promoter is methyl iodide.

4. The process of claim 1 wherein the heterocyclic aromatic amine promoter is selected from the group consisting of pyridine, 4-picoline, 4-ethylpyridine, 2-picoline and purine.

5. The process of claim 1 wherein the heterocyclic aromatic amine promoter is 4-picoline.

6. The process of claim 1 wherein preferred soluble Group VIII metal catalysts are selected from the group consisting of halides, carboxylates, nitrates and carbonyls of cobalt, ruthenium and nickel.

7. The process of claim 1 wherein the soluble Group VIII metal catalyst is selected from the group consisting of carbonyl containing compounds of ruthenium, cobalt and nickel.

8. The process of claim 1 wherein the carbon monoxide gas is mixed with an inert gas.

9. The process of claim 1 wherein the concentration of the halide or aromatic amine promoter is from 1-20 mole %.

10. The process of claim 1 wherein the protonic coreactant is selected from the group consisting of methanol and water.

11. The process of claim 1 wherein the concentration of the soluble Group VIII metal catalyst is from 5-200 ppm.

12. The process of claim 1 wherein the carbon bed is an activated carbon bed.

13. The process of claim 1 wherein the mole ratio of Group VIII metal containing catalyst to promoter to protonic coreactant is 1:1000:1000 to 1:10,000:30,000.

14. A process for the continuous production of acids and esters which comprises passing liquid feed consisting of a an olefin, a halide promoter, a protonic coreactant from the group consisting of alcohols and water and a soluble Group VIII metal catalyst, wherein, the metal catalyst concentration ranges from 1 ppm to greater than 1000 ppm optionally in the presence of a solvent and a gas comprising carbon monoxide over a carbon bed maintained at a temperature of 225° C. to 350° C. and a pressure of from about 500 psi to 4000 psi.

15. The process of claim 14 wherein the soluble Group VIII metal catalysts are selected from the group consisting of halides, carboxylates, nitrates and carbonyls containing cobalt, rithenium, iron, nickel, rhodium, palladium, osmium, iridium and platinum.

16. A process for the continuous production of isobutyric acid and n-butyric acid and the respective esters along with acetic acid and methyl alcohol which comprises passing a liquid feed consisting of propylene, a soluble Group VIII containing metal catalyst from the group consisting of ruthenium chloride, triruthenium dodecacarbonyl and dicobalt octacarbonyl, a promoter selected from the group consisting of a lower alkyl iodide or a heterocyclic aromatic amine, a protonic coreactant from the group consisting of methanol or water, optionally a solvent and a gas consisting of carbon monoxide into a reactor over an activated carbon bed having a density range of 0.03-2.5 g/$cm^3$ and a surface area of 200-2000 $m^2$/g, wherein the mole ratio of Group VIII containing metal catalyst to promoter to protonic coreactant is 1:1000:1000 to 1:10,000:30,000, and the concentration of the solbule metal catalyst is from 5-200 ppm, and reacting the liquid feed at a temperature of 225° C. to 350° C. and a pressure of 500 psi to 4000 psi.

17. The process of claim 16 wherein the soluble Group VIII containing metal catalyst is triruthenium dodecacarbonyl, the promoter is methyl iodide and the protonic coreactant is methanol.

* * * * *